United States Patent [19]

Williams et al.

[11] Patent Number: 4,833,131

[45] Date of Patent: May 23, 1989

[54] SOLUBLE PHOSPHORYLATED GLUCAN: METHODS AND COMPOSITIONS FOR WOUND HEALING

[75] Inventors: David L. Williams, River Ridge; I. William Browder, New Orleans, both of La.

[73] Assignee: Bioglucans, L.P., New Orleans, La.

[21] Appl. No.: 12,963

[22] Filed: Feb. 10, 1987

Related U.S. Application Data

[63] Continuation-in-part of Ser. No. 767,388, Aug. 19, 1985, Pat. No. 4,739,046.

[51] Int. Cl.$^4$ .............. A61K 9/06; A61K 31/715
[52] U.S. Cl. .................... 514/54; 514/61; 536/1.1; 536/117; 536/124
[58] Field of Search ............ 536/1.1, 117, 124; 514/61, 54

[56] References Cited

U.S. PATENT DOCUMENTS

| | | |
|---|---|---|
| 3,081,226 | 3/1963 | DiLuzio .................. 514/61 |
| 3,396,082 | 8/1968 | Davis et al. ............. 536/1.1 |
| 4,138,479 | 2/1979 | Truschiet et al. ........ 424/88 |
| 4,202,966 | 5/1980 | Misaki et al. ........... 536/1.1 |
| 4,225,673 | 9/1980 | Sugiura et al. .......... 435/101 |
| 4,237,266 | 12/1980 | Sugiura et al. ......... 536/1 |
| 4,340,673 | 7/1982 | Stoudt et al. ........... 536/1.1 |
| 4,396,611 | 9/1983 | Ducan .................... 536/1.1 |
| 4,493,894 | 1/1985 | Miyashiro et al. ....... 435/101 |

OTHER PUBLICATIONS

Bärlin et al., in Heterogeneity of Mononuclear Phagocytes, Forster & Landy, eds., Academic Press, New York, pp. 243-252 (1981).
Chesterman et al., Toxicol. Lett. 9: 87-90 (1981).
Chirigos et al., Cancer Res. 38: 1085-91 (1978).
Cozens et al., Toxicol. Lett. 9: 55-64 (1981).
Deimann and Fahimi, J. Exper. Med. 149: 883-97 (1979).
DiLuzio and Riggi, J. Reticuloendothel. Soc. 8: 465-73 (1970).
DiLuzio, Trends in Pharmacol. Sci. 4: 344-47 (1983).
DiLuzio et al., Int'l J. Cancer 24: 773-779 (1979).
Ehrke et al., Int'l J. Immunopharm. 5: 34-42 (1983).
Glovsky et al., J. Reticuloendothel. Soc. 33: 401-13 (1983).
Hassid et al., J. Amer. Chem. Soc. 63: 295-98 (1941).
Holbrook et al., Am. J. Trop. Med. Hyg. 30: 762-68 (1981).
Liu et al., Life Sci. 29: 1027-32 (1981).
Mansell and DiLuzio, in the Macrophage in Neoplasia, Fink, ed., Academic Press, New York, pp. 227-243 (1976).
Niskanen et al., Cancer Res. 38: 1406-09 (1978).
Patchen, Surv. Immunol. Res. 2: 237-42 (1983).
Patchen et al., J. Biol. Res. Mod. 3: 627-633 (1984).
Patchen and Lotzova, Exper. Hematol. 8: 409-22 (1980).
Riggi and DiLuzio, Am. J. Physiol. 200: 297-300 (1961).
Saito, Carbohydrate Res. 58: 293-305 (1977).
Seljelid et al., Exper. Cell Res. 131: 121-29 (1981).

(List continued on next page.)

Primary Examiner—Roland W. Griffin
Attorney, Agent, or Firm—Pennie & Edmonds

[57] ABSTRACT

A new class of soluble phosphorylated glucans is described as well as the process for making the same. According to one embodiment, the soluble phosphorylated glucan is derived from the Yeast *Saccharomyces cerevisiae*. The soluble phosphorylated glucans are useful for promoting the wound healing process. The soluble phosphorylated glucans are also useful for prophylactic and therapeutic applications against neoplastic, bacteria, viral, fungal and parasitic diseases. The soluble phosphorylated glucans are used either alone or in combination with a known antimicrobial agent for prophylactic and therapeutic antimicrobial applications. Additionally, they may be administered either alone or as a non-toxic adjuvant, in combination with chemotherapy. The soluble phosphorylated glucans are also useful for stimulating macrophage cells, either in vivo or in vitro, to produce a cytotoxic/cyctostatic factor effective against cancer cells.

10 Claims, 1 Drawing Sheet

OTHER PUBLICATIONS

Schultz et al., in Immune Modulation and Control of Neoplasia by Adjuvant Therapy, Chirigos, ed., Raven Press, New York, pp. 241–248 (1978).
Suziuki et al., Gann 60: 273–77 (1969).
Williams et al., Hepatol. 5: 198–205 (1985).
Williams et al., Curr. Chemother. and Infectious Disease, Proc. 11th ICC and 19th ICAAC, pp. 1724–1726 (1980).
Wooles and DiLuzio, Proc. Soc. Exper. Biol. Med. 115: 756–59 (1964).
Yamamura and Azuma, Adv. Immunopharm. 2: 501–07 (1982).
Chihara, Rivista di Immunolog. ed Immunofarm. 5(2): 97–85 (1983).
Song and DiLuzio, in Lysosomes in Biology and Pathology, Dingle et al., eds., 6: 533–47 (1979).
Yosida et al., Adv. Pharmacol. Ther. II 6: 101–12 (1982).
DiLuzio and Williams, in Chemical Regulation of Immunology in Veterinary Medicine, Alan R. Liss, Inc., pp. 443–456 (1984), entitled "The Roll of Glucan in the Prevention and Modification of Microparasitic Diseases".
DiLuzio et al., in The Macrophage in Neoplasia; Academic Press, Inc. New York, pp. 181–198 (1976), entitled "The Employment of Glucan and Glucan Activated Macrophages in the Enhancement of Host Resistance to Malignancies in Experimental Animals".
DiLuzio and Chihara, in Advances in Immunopharmacology Hadden et al., eds., Pergamon Press Oxford and New York, pp. 477–484 (1980).
Browder et al., Int. J. Immunopharmac. 6: 19–26 (1984), entitled "Modification of Post-Operative C. Albicas Sepsis by Glucan Immunostimulation".
Jacques, in Current Concepts in Human Immunology and Cancer Immunomodulation, Serron et al., eds., Elsevier Biomedical Press BV, pp. 429–438 (1982), entitled "Immunomodulator Polysaccharides".
Mansell et al., in Immune Modulation and Control of Neoplasia by Adjuvant Chirigos eds., Raven Press, Inc., pp. 255–280 (1978).
Aoki, in Immunomodulating Agents: Properties and Mechanisms, Chirigos, eds., Marcel Dekker, 20: 63–77 (1984).
Hamuro et al., in Immunomodulating Agents: Properties and Mechanisms, Chirigos, ed. Marcel Dekker, Inc., 20: 409–36 (1984).
Ashworth et al., Exper. Molec. Pathol. Supp. 1: 83–103 (1963), entitled "A Morphologic Study of the Effect of Reticuloendothealial Stimulation upon Hepatic Removal of Minute Particles from the Blood of Rats".
Riggi and DiLuzio, Nature 193: 1292–94 (1962), entitled "Hepatic Function During Reticuloendothelial Hyperfunction and Hyperplasia".
Wooles et al., Rad. Res. 16: 546–54 (1962) entitled "Influence of Pre- and Post-X-Irridation Zymosan Administration on Reticuloendothelial Function".
Bomford and Moreno, Br. J. Cancer 36: 41–48 (1977), entitled "Mechanisms of the Anti-Tumor Effect of Glucans and Fructosans: A Comparison with C. Parrvum".
Burgaleta and Golde, Cancer Res. 37: 1739–42 (1977), entitled "Effect of Glucan on Granulopoiesis and Macrophage Genesis in Mice".
DiLuzio, in Kupffer Cells and Other Liver Sinusoidal Cells, Wisse and Knook eds., Elsevier Amsterdam, pp. 397–306 (1977).
DiLuzio et al., in The Macrophage and Cancer, James et al., eds., Edinburgh Univer. Med. Pres., pp. 181–901 (1977).
Schultz et al., Cancer Res. 37: 3338–43 (1977), entitled "Association of Macrophage Activation with Anti-Tumor Activity by Synthetic and Biologic Agents".
DiLuzio and Williams, Infection and Immun. 20: 804–10 (1978), entitled "Protective Effect of Glucan Against Systemic *Staphylococcus aureus* Septicemia in Normal and Leukemic Mice".
Wooles and DiLuzio, J. Reticuloendothelial. Soc. 1: 160–69 (1964); entitled "The Phagocytic and Proliferative Response of the Reticuloendothelial System Following Glucan Administration".
Browder et al., in Immunomodulation by Microbial Products and Related Synthetic Compounds, Yamamura et al., eds. Excerpta Medica, Amsterdam, pp. 354–357 (1982).
Cook et al., Infect. Immun. 37: 1261–69 (1982) entitled "Protective Effect of Glucan Against Visceral Leishmaniasis in Hamsters".
Song and DiLuzio, in Lysosomes in Biology and Pathology, Dingle et al., eds. North Holland Press Amsterdam 6: 533–47 (1979).

(List continued on next page.)

OTHER PUBLICATIONS

Popisil et al., Experientia 38: 1232–34 (1982) entitled "Glucan Induced Enhancement of Hemopoietic Recovery in Gamma-Irradiated Mice".

Sasaki et al., J. Pharm. Dyn. 5: 1012–16 (1982), entitled "Effect of Serum from Mice Treated with Antitumor Polysaccharide on Expression of Cytotoxicity by Mouse Periotoneal Macrophages".

Satoh et al., J. Pharm. Dyn. 5: 818–28 (1982), entitled "Elevation of Colony Stimulating Factors in Mouse Serum after Injection of PSK, an Antitumor Polysaccharide".

Jacques et al., in Sinusoidal Liver Cells, Knook et al., eds., Elsevier Biomedical Press, pp. 479–481 (1982).

DiLuzio et al., J. Reticuloendothelial Soc. 7: 731–42 (1970); entitled "Evaluation of the Mechanism of Glucan-Induced Stimulation of the Reticuloendothelial System".

Mansell et al., J. Nat'l Cancer Inst. 54: 571–80 (1975) entitled "Macrophage-Mediated Destruction of Human Malignant Cells in vitro".

Inai et al., J. Immunol. 117: 1256–60 (1976), entitled "Activation of the Alternative Complement Pathway by Water-Insoluble Glucans of Streptococcus mutans: the Relation between their Chemical Structures and Activating Potencies".

Proctor et al., J. Immunopharmacol. 3: 385–94 (1981–82) entitled "Development of a Bioassay for Anti-Tumor Activity of Biological Response Modifers of the Reticuloendoethelial Stimulant Class: Reproducibility of the Bioassay".

Bogwald et al., Scand. J. Immuol. 15: 297–04 (1982) entitled "The Cytotoxic Effect of Mouse Macrophages Stimulated in vitro by a Beta-1,3-D-Glucan from Yeast Cell Walls".

Williams et al., J. Reticuloendothel. Soc. 23: 479–90 (1978), entitled "Protective Effect of Glucan in Experimentally Induced Candidiasis".

Stewart et al., Cancer Treat. Prep. 62: 1867–72 (1978), entitled "Preliminary Observations on the Effect of Glucan in Combination with Radiation and Chemotherapy in Four Murine Tumors".

Kohl et al., J. Immunol. Methods 29: 361–368 (1979) entitled "Inhibition of Human Monocyte-Macrophage and Lymphocyte Cytotoxicity to Herpes-Simplex-Infected Cells by Glucan".

Lahnborg et al., Eur. Surg. Res. 14: 401–08 (1982) entitled "Glucan-Induced Enhancement of Host Resistance in Experimental Intraabdominal Sepsis".

Lahnborg et al., J. Reticuloendothel. Cos. 32: 347–53 (1982) entitled "The Effect of Glucan-A Host Resistance Activator and Ampicillin on Experimental Intraabdominal Sepsis".

Kimura et al., J. Reticuloendothel. Soc. 34: 1–11 (1983), entitled "In vitro Activation of Human Adherent Cells by a Glucan, Schizophyllan".

Mashiba et al., Japan J. Exp. Med. 53: 195–98 (1983), entitled "In vitro Activation of Human Adherent Cells by a Glucan Schizophyllan".

Williams and DiLuzio, Science 208: 67–69 (1980), entitled "Induced Modification of Murine Viral Hepatitis".

Proctor and Yamamura, J. Nat'l Cancer Inst. 61: 1179–80 (1978); entitled "Letter to the Editor: Effectiveness of Glucan in the Treatment of Human Neoplasia".

Sasaki et al., Cancer Res. 38: 379–83 (1978), entitled "Dependence on Chain Length of Antitumor Activity of (13)-Beta-D-Glucan from *Alcaligenes faecalis* var. *myxogenes* IFO13140, and its Acid-Degraded Products".

DiLuzio and Williams, Cancer Immunol. Immunother. 6: 73–9 (1979), entitled "Glucan-Induced Modification of the Increased Susceptibility of Cyclophosphamide-Treated Mice to Staphylococcus aureus Infection".

Lotzova and Gutterman, J. Immunol. 123: 607–11 (1979), entitled "Effect of Glucan on Natural Killer (NK) Cells: Further Comparison Between NK Cell and Bone Narrow Effector Cell Activities".

Delville et al., Acta Leprologica 77/76: 273–81 (1979), entitled "Le-beta 1,3-Glucan et Autres Immunomodulateurs dans l'Infection lepresis Experimentale Chez la Souris".

Nuyen and Stadtsbaeder, in Advances in Exper. Med. and Biology, vol. 121A Escobar and Friedman, eds. Plenum Press, New York, pp. 255–66 (1980), entitled "Comparative Biological and Antitoxoplasmic Effects of Polysaccharides In vitro".

Gillet et al., in Advances in Exper. Med. and Biology, vol. 121A, Escobar and Friedman, eds., Plenum Press, New York, pp. 307–313 (1980), entitled "Particulate beta 1-3 Glucan and Casual Prophylaxis of Mouse Malaria (Plasmodium berghei(".

(List continued on next page.)

OTHER PUBLICATIONS

Leibovich et al., J. Reticuloendothel. Soc. 27: 1–11 (1980), entitled "Promotion of Wound Repair in Mice by Application of Glucan".

Cook et al., J. Reticuloendothel. Soc. 27: 567–73 (1980), entitled "Visceral Leishmaniasis in Mice: Protective Effect of Glucan".

Williams and DiLuzio, in the Reticuloendothelial System and Pathogenesis of Liver Disease, Liehr and Grun eds., Elsevier/North Holland Biomedical Press, pp. 363–368 (1980), entitled "Modification of Experimental Viral Hepatitis by Glucan Induced Macrophage Activation".

Browder et al., J. Surg. Res. 35: 474–79 (1983), entitled "Protective Effect of Nonspecific Immunostimulation in Post Splenectomy Sepsis".

Bogwald et al., J. Leucyte Biol. 35: 357–71 (1984), entitled "Lysosomal Glycosidase in Mouse Peritoneal Macrophages Stimulated In Vitro With Soluble and Insolubel Glycans".

Cook et al., Surv., Immunolog. Res. 2: 243–45 (1983), entitled "Immunomodulation of Protozoan Diseases".

Seljelid et al., Immunopharmacol. 7: 69–73 (1984), entitled "A Soluble beta-1,3-D-Glucan Derivative Potentiates the Cytostatic and Cytolytic Capacity of Mouse Peritoneal Macrophages In Vitro".

Suga et al., Cancer Res. 44: 5132–37 (1984), entitled "Antitumor Activity of Lentinan in Murine Syngeneic and Autochthonons Hosts and its Suppressive Effect on 3-Methylcholanthrene-induced Carcinogenesis".

Deslandes et al., Macromolecules 13: 1466–71 (1980), entitled "Triple-Helical Structure (1 3)-beta-D-Glucans".

Sarko et al., Biochem. Soc. Trans. 11: 139–42 (1983), entitled "Multiple-Helical Glucans".

Yanki et al., Biophys. Chem. 17: 337–42 (1983), entitled "Correlation Between the Antitumor Activity of a Polysaccharide Schizophyllan and its Triple-Helical Conformation in Dilute Aqueous Solution".

Sasaki et al., Cancer Treat. Rep. 67:275–80 (1983), entitled "Antitumor Activity of Tetrahydro-2-furanyl-and tetrahydro-2-pyranyl-Glucans Obtained by Chemical Modification of (1 3)-beta-D-Glucan from *Alcaligenes faecalis* var. myxogenes IFO 13140 and its Lower Molecular Weight Glucans".

Hunt et al., 1984, Surgery 96:48–54.

Israel and Edelstein, 1978, in "Immune Modulation and Control of Neoplasia," Chirigos, ed., Raven Press, N.Y. pp. 255–80.

Kenyon, 1983, Am. J. Vet. Res. 44: 652–56.

Kenyon et al., 1985, Lab. Animal Sci. 35:150–52.

Leibovich et al., 1975, Am. J. Pathol 78:71–100.

Mansell and DiLuzio, 1976, in "The Macrophage in Neoplasia", Fink, ed., Academic Press, New York, pp. 227–43.

Orita et al., 1986, Am. J. Obstet. Gynecol. 155:905–11.

Simpson and Ross, 1971, Am. J. Pathol. 65:49.

Wolk et al., 1985, Med. Biol. 63:73–80.

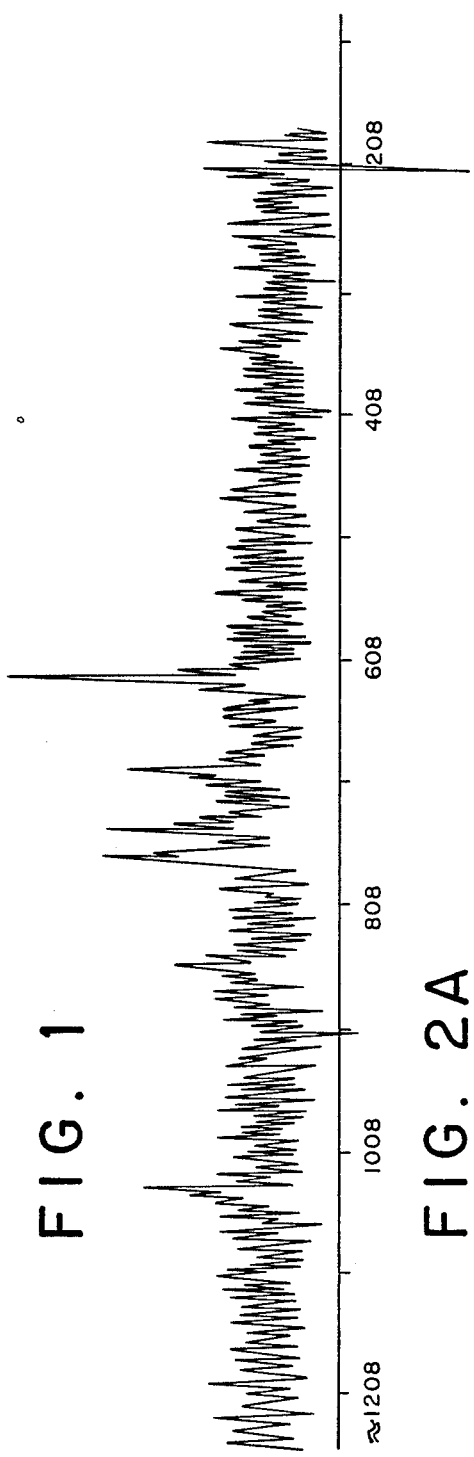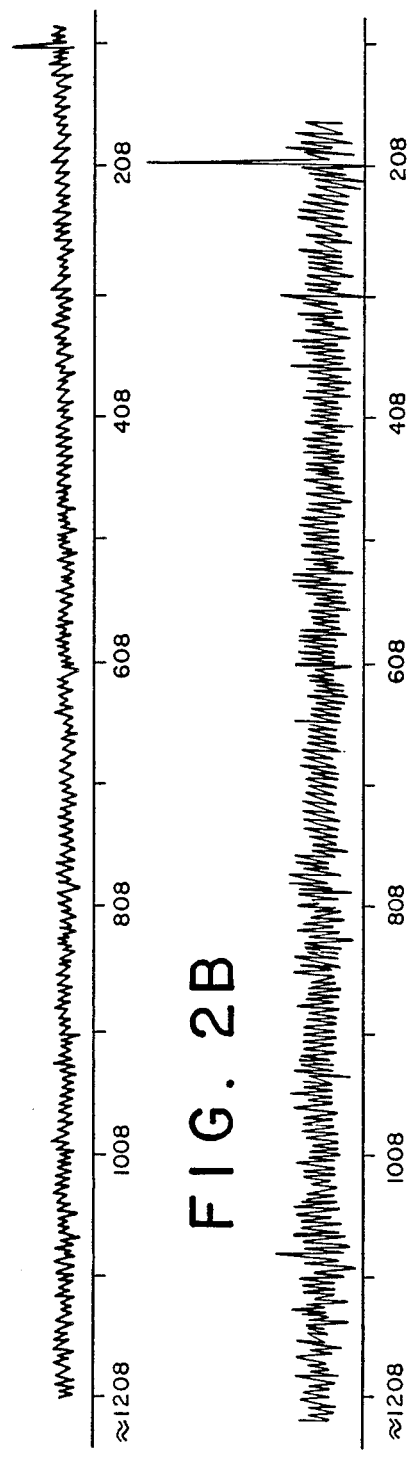

SOLUBLE PHOSPHORYLATED GLUCAN: METHODS AND COMPOSITIONS FOR WOUND HEALING

CROSS REFERENCE TO RELATED APPLICATION

This application is a continuation-in-part of application Ser. No. 767,388 filed on Aug. 19, 1985, now U.S. Pat. No. 4739,046 issued Apr. 19, 1988.

TABLE OF CONTENTS

1. Field of the Invention
2. Background of the Invention
   2.1 Immunobiological Activity of Particulate Glucans
      2.1.1 Particulate Glucans and Wound Healing
   2.2. Adverse Side Effects of Particulate Glucans
   2.3. Unsuccessful Attempts To Solubilize Particular Glucans
3. Summary of the Invention
4. Brief Description of the Figures
5. Detailed Description of the Invention
   5.1. Process For Preparation of Soluble Phosphorylated Glucan
   5.2. Characterization of Soluble Phosphorylated Glucan
      5.2.1. Elemental Composition
      5.2.2. Structural Configuration
         5.2.2.1. Molecular Sieving
         5.2.2.2. Nuclear Magnetic Resonance Spectroscopy
   5.3. Non-Toxicity, Non-Pyrogenicity Non-Immunogenicity of Soluble Phosphorylated Glucan
      5.3.1. Non-Toxicity
      5.3.2. Non-Pyrogenicity
      5.3.3. Non Immunogenicity
   5 4. Applications For Wound Healing
   5.5. Routes and Methods of Administration
6. Preparation of Soluble Phosphorylated Glucans
   6.1. Preparation From Particulate Glucan Obtained From Saccharomyces
   6.2. Preparation From Coriolus Verisicolor
   6.3. Preparation From Sclerotium
7. Promotion of Healing Surgical Wounds
   7.1 Topical Administration of Soluble Phosphorylated Glucan
   7.2. Systemic Administration of Soluble Phosphorylated Glucan
8. Enhancement of Macrophage Phagocytic Activity

1. FIELD OF THE INVENTION

This invention is related to pharmaceutical compositions and methods for the promotion of wound healing. In particular, the invention relates to compositions and methods to promote wound healing which utilize a novel class of soluble phosphorylated glucans in which the poly-[beta-(1-3)glucopyranose] chains are phosphorylated in varying degrees.

2. BACKGROUND OF THE INVENTION

The term "glucan" refers generically to a variety of naturally occurring homopolysaccharides or polyglucoses, including polymers such as cellulose, amylose, glycogen, laminarians, starch, etc. Glucan encompasses branched and unbranched chains of glucose units linked by 1-3, 1-4, and 1-6 glucosidic bonds that may be of either the alpha or beta type.

As defined herein, "particulate glucan" designates a water-insoluble particulate (about 1-3 u) polyglucose such as that derived from the cell wall of the yeast *Saccharomyces cerevisiae*. Particulate glucan is macromolecular and comprises a closed chain of glucopyranose units united by a series of beta-1-3 glucosidic linkages. (Hassid et al., 1941, J. Amer. Chem. Soc. 63: 295-298; Di Luzio et al., 1979, Int'l J. Cancer 24: 773-779). X-ray diffraction studies have demonstrated that particulate glucans exist in the form of a triple-stranded helices. (Sarko et al., 1983, Biochem. Soc. Trans. 11: 139-142).

2.1. IMMUNOBIOLOGICAL ACTIVITY OF PARTICULATE GLUCANS

Particulate glucan is a potent activator of the macrophage/monocyte cell series, complement, as well as of B cell lymphocytes. Thus, particulate glucan has profound effects on both the reticuloendothelial and immune systems.

Previous studies have demonstrated that in vivo administration of particulate glucan to a variety of experimental animals induces a number of profound immunobiological responses, including the following: (1) enhanced proliferation of monocytes and macrophages (Deimann and Fahimi, 1979, J. Exper. Med. 149: 883-897; Ashworth et al., 1963, Exper. Molec. Pathol., Supp. 1: 83-103); (2) enhanced macrophage phagocytic function (Riggi and Di Luzio, 961, Am. J. Physiol. 200: 297-300); (3) enhanced macrophage secretory activity (Bärlin et al., 1981, in Heterogeneity of Mononuclear Phagocytes, Forster and Landy, eds., Academic Press, New York, pp. 243-252); (4) increased macrophage size (Patchen and Lotzova, 1980, Exper. Hematol. 8: 409-422); (5) enhanced macrophage adherence and chemotactic activity (Niskanen et al., 1978, Cancer Res. 38: 1406-1409); and (6) enhanced complement activation (Glovsky et al., 1983, J. Reticuloendothel. Soc. 33: 401-413). Increased cytolytic activity against tumor cells has been demonstrated in macrophages from animals and man treated with particulate glucan both in vivo (Mansell and Di Luzio, 1976, in "The Macrophage in Neoplasia", Fink, ed., Academic Press, New York, pp. 227-243) and in vitro (Chirigos et al., 1978, Cancer Res. 38: 1085-1091).

Stimulation of the reticuloendothelial system by in vivo administration of particulate glucan leads to inhibition of allogenic or xenogenic bone marrow graft acceptance in lethally irradiated animals. (See, e.g., Wooles and Di Luzio, 1964, Proc. Soc. Exper. Biol. Med. 115: 756-759). This finding denotes that glucan will induce host defense mechanisms even against normal cells if they are genetically different from the host.

In addition to effects on reticuloendothelial and immune responses, in vivo administration of particulate glucan has been demonstrated to enhance hemopoietic activity including granulopoiesis, monocytopoiesis and erythropoiesis leading to greater recovery from a lethal dose of whole body irradiation (Patchen, 1983, Surv. Immunol. Res. 2: 237-242).

A number of studies have indicated that in vivo administration of particulate glucan significantly modifies host resistance to a wide variety of infectious diseases induced by bacterial, fungal, viral and parasitic organisms. In particular, enhanced host resistance to infection has been shown when animals are challenged by microorganisms such as *Eshericheria coli, Staphylococcus aureus, Francisella tularensis, Mycobacterium leprae, Streptococcus pneumoniae, Candida albicans, Sporotrichum schenckii*, as well as viruses such as Venezuelan equine encephalomyelitis virus, Rift Valley fever virus, murine hepatitis virus, frog virus III, Herpes simplex I and II, and parasites such as *Leishmania donovani* (see review by Di Luzio, 1983, Trends in Pharmacol. Sci. 4: 344–347 and references cited therein).

Extensive studies have indicated that particulate glucan has potent anti-tumor activity. For example, particulate glucan has been shown to inhibit tumor growth and prolong survival in four syngeneic murine tumor models including adenocarcinoma BW 10232, an plastic carcinoma 15091A, melanoma B16, and spontaneous lymphocytic leukemia BW5147 (Di Luzio et al, 1979, in Advances in Experimental Medicine and Biology, Vol. 121A: 269–290).

To evaluate the cellular basis of the anti-tumor activity of particulate glucan, the anti-tumor cytotoxic activity of peritoneal macrophages, derived from control and particulate glucan-treated mice, was studied (Mansell and Di Luzio, 1976, in The Machrophage in Neoplasia, Fink, ed. Academic Press, New York, pp. 227–243). These studies indicated that peritoneal macrophages from glucan-treated mice produced a significant cytotoxic response compared to normal macrophages. This observation has been confirmed (See, e.g., Bärlin et al. 1981, in Heterogenity of Mononuclear Phagocytes, Forster and Landy, eds., Academic Press, New York, pp. 243–252) and Chirigos et al., 1978, Cancer Res. 38: 1085–1091).

Additionally in vitro studies using normal and tumor cells incubated with particulate glucan have demonstrated that glucan exerts a direct cytostatic effect on sarcoma and melanoma cells and a proliferative effect on normal spleen and bone marrow cells (Wiliiams et al., 1985, Hepatology 5: 198–206). These studies indicate that glucan, when administered therapeutically, will (1) significantly inhibit hepatic metastases; (2) inhibit the growth of the primary tumor; and (3) enhance survival, possibly by increased Kupffer cell tumoricidal activity as well as by a direct cytostatic effect of such glucan on sarcoma cells.

2.1.1. PARTICULATE GLUCANS AND WOUND HEALING

As used throughout the present specification, "wound healing" refers to the totality of processes culminating in the closure of wounds and ulcers. Wound healing encompasses a number of aspects including, but not limited to increases in: macrophage infiltration, fibroplasia, wound debridement, angiogenesis, collagen synthesis and tensile strength, etc. The central role of the macrophage in wound healing or repair has been extensively investigated (See e.g., Orita et al., 1986, Am. J. Obstet. Gynecol. 155: 905–11; Wolk et al., 1985, Med. Biol. 63: 73–80; Hunt et al., 1984 Surgery 96: 48–54).

Studies by Simpson and Ross (1971, Am. J. Pathol. 65: 49) demonstrated that depletion of neutrophils from the wound site did not adversely affect the healing process. They concluded that the neutrophil, while critical to infectability of the wound, was not essential for fibrinogenesis. On the other hand, studies have indicated that the macrophage cell is primarily responsible for debridement and, perhaps, stimulation of fibroblast accumulation and proliferation at the wound site. In 1975, Leibovich et al., (1975, Am. J. Pathol. 78: 71–100) induced almost complete disappearance of macrophages from the site of an experimentally induced wound by the conjoint administration of hydrocortisone and anti-macrophage serum to guinea pigs. The removal of fibrin and other debris from the wound area was significantly delayed following such immunosuppressive treatment. Additionally, fibroblasts did not appear at the wound site as quickly as in the controls; the rate of fibroblast proliferation was substantially reduced in the macrophage-depleted animals. The observations of Leibovich et al., have been confirmed and extended by Hunt and co-workers (1984, Surgery 96: 48–54) who noted that macrophages stimulated not only fibroplasia and collagen synthesis, but also induced angiogenesis during the process of wound healing. More importantly, they observed that treatment of macrophages with lipopolysaccharide increased their capacity to stimulate collagen synthesis and angiogenesis, thus demonstrating that tissue injury is not a maximal stimulus for wound repair.

As detailed above herein, particulate glucan is a potent activator of macrophage cells as well as a potent inducer of non-specific host defense mechanisms. Particulate glucan-induced macrophage activation has been implicated in promoting of wound healing (Mansell and DiLuzio 1976, in "The Macrophage in Neoplasia", Fink, ed. Academic Press, New York, pp.227–243). In these studies, particulate glucan was administered topically or intralesionally to individuals with ulcerative malignant lesions. Mansell and DiLuzio observed that particulate glucan "promptly healed the malignant ulcer", even in cases where the lesion had not responded to chemotherapy (Mansell and DiLuzio, supra). It is important to note that the topical or intralesional administration of glucan resulted in macrophage recruitment and activation with a concomitant destruction of malignant cells, but normal tissue in close proximity to the lesion was not altered. Subsequent studies by Israel and Edelstein confirmed and extended the observations of Mansell and DiLuzio noting not only resolution of treated lesions, but also disappearance of a distant cutaneous malignant lesion (1978, in "Immune Modulation and Control of Neoplasia," Chirigos, ed., Raven Press, New York, pp. 255–280). This observation suggests a potential systemic effect following intralesional administration particulate glucan.

Leibovich et al., (1980, J. Reticuloendothel. Soc. 27:1–11) examined the influence of topical administration of particulate glucan and other agents (i.e., carrageenan, levan, inulin, dextran, starch and talcum powder) on experimental wound healing in mice. Of all the agents stddied, only particulate glucan had any marked beneficial effect on healing. Wounds treated with particulate glucan showed a higher number of macrophages in the early stages of repair as well as earlier complete reepithelization and onset of fibroplasia when compared to those of control animals (Leibovich et al., supra). The appearance of fibroblasts in animals treated with particulate glucan was also more prominent (Id.). In summary, topical administration of particulate glucan resulted in the activation and recruitment of macrophages to the wound area, which subsequently enhanced proliferation of fibroblasts and capillaries culminating in accelerated healing of the wound. (Id.).

Studies by Kenyon [(1983, Am. J. Vet. Res., 44: 652–56) hereinafter "Kenyon I" ] and Kenyon et al., [(1985, Lab. Animal Sci., 35: 150–52) hereinafter "Kenyon II"] have examined the effect of topical particulate glucan administration on wound healing in animals with defective macrophage function. Kenyon I observed that mice acutely or chronically infected with Sendai virus which characteristically depresses macrophage functional activity had impaired healing of experimental wounds. Such impaired wound healing could be overcome by topical administration of particulate glucan. More recently, Kenyon II demonstrated that mice with a genetically-induced macrophage dysfunction exhibited decreased wound healing when compared to mice with normal macrophage function. The wound breaking strength observed in mice with genetically-linked macrophage dysfunction was restored to normal by the topical administration of particulate glucan (Kenyon II, supra).

Notwithstanding these biological properties, the adverse side effects of particulate glucans have made these compounds all but useless in clinical medicine.

2.2. ADVERSE SIDE EFFECTS OF PARTICULATE GLUCANS

When particulate glucan is administered in vivo to animals, a number of severe side effects have become apparent, the most notable being:
(1) formation of granuloma;
(2) development of hepatosplenomegaly;
(3) increased susceptibility to endotoxin;
(4) activation of complement (anaphylyotoxin);
(5) development of pulmonary granulomatous vasculitis;
(6) development of hypotension following intravenous administration; and
(7) development of microembolism when administered a high concentrations.

Additionally, there is a relatively high degree of acute toxicity observed when particulate glucan is administered in vivo. For example, following a single intravenous injection of an aqueous suspension of particulate glucan, 20% and 100% mortality were observed in mice receiving glucan at 250 and 500 mg/kg body weight respectively.

Moreover, due to the particulate nature of the glucan preparation (1–3 u), it is difficult to administer via an intravenous route. By way of illustration, one patient receiving particulate glucan required constant supervision during intravenous (IV) administration, continuous shaking of the IV drip bottle being essential to maintain the particulate glucan in suspension to avoid formation of emboli in the patient.

Although slightly soluble neutral glucans are commercially available, these preparations are not suitable for intravenous administration because the aqueous solutions have very high viscosity and, more importantly, because their use when administered to experimental animals has inevitably been accompanied by considerable toxicity.

Lentinan, a high molecular weight and poorly soluble beta-1,3 and beta-1,6 glucan obtained from *Lentinus edodes*, has been studied following intravenous administration to dogs. A variety of adverse clinical effects were observed following administration of lentinan (Ajinomoto Co. Inc., Tokyo, Japan) at doses of 2.0, 8.0 and 30 mg/kg/day for 5 weeks. Adverse effects included vomiting, erythema, discoloration of the sclera, and facial swelling. Circulatory collapse, unsteady gait, altered behavioral patterns, excessive salivation were also seen in individual beagles. At autopsy, congestion of the gastrointestinal mucosa was observed in animals treated with 2.0 or 8.0 mg/kg/day. Morphological changes of liver indicated intracytoplasmic material, possibly lentinan, accumulating in liver cells. One animal showed circulatory collapse upon the first injection at 8.0 mg/kg. While he did recover, the animal experienced repeated vomiting episodes with presence of blood indicating hemorrhaging of the gastrointestinal tract. Another animal appeared to show a marked allergic response, as demonstrated by erythema and subcutaneous swelling (edema) of the face. Autopsy findings demonstrated extensive edema of subcutaneous tissue, and congestion of the gastrointestinal tract with hemorrhaging. Macrophage cells showed accumulation of material, possibly lentinan. (Chesterman et al., 1981, Toxicol. Lett. 9: 87–90).

Additional toxicity studies were performed in which a variety of doses of lentinan ranging from 0.1 to 1.0 mg/kg/day were given intravenously to rats for 9 weeks. Toxicity was manifested by the development of cutaneous lesions and discoloration of the ears suggesting thromboembolic events. (Cozens et al., 1981, Toxicol. Lett. 9: 55–64).

2.3. UNSUCCESSFUL ATTEMPTS TO SOLUBILIZE PARTICULATE GLUCANS

In view of these disadvantages of particulate beta-1,3 glucans for in vivo administration, extensive studies were undertaken to develop a soluble beta-1,3 polyglucose which might be non toxic, induce no significant pathology, and yet retain significant immunobiological activity.

A low molecular weight non-phosphorylated soluble glucan preparation prepared by formic acid hydroylsis of particulate glucan has been shown to have anti-tumor and anti-staphylococcal activity (Di Luzio et al., 1979, Internat'l J. Cancer 24: 773–779). Unfortunately, the low yield and diversity of fractions obtained by this method made this preparation non-useful for prophylactic and therapeutic applications. (See Di Luzio, 1983, Trends in Pharmacological Sciences 4: 344–347).

Similarly, attempts to solubilize particulate glucan by the addition of dimethylsulfoxide (DMSO) a "molecular relaxant" were also unsuccessful. It was thought the DMSO would "relax" the triple helical configuration of the glucan molecule. Indeed, particulate glucan dissolves in the presence of DMSO. All attempts to isolate a soluble glucan from the DMSO solution, however, resulted in failure. Upon dilution of the DMSO-glucan solution with various aqueous media such as glucose or saline solutions, the particulate glucan was reformed. Following dilution of the DMSO-soluble glucan solution with saline, all animals receiving injections of these solutions died immediately upon injection due to high concentration of DMSO or the reformation of the particulate glucan. Upon precipitation of the glucan in DMSO solution by the addition of ethanol (100%), the precipitate was collected and lyophilized. When this lyophilized glucan was added to water, the particulate glucan reformed.

Attempts to convert the neutral glucan preparation of particulate glucan to a polar-charged preparation by the addition of phosphate or sulfate groups as well as by acetylation were also unsuccessful. Each of these procedures was conducted following the solubilization of particulate glucan by DMSO and in each instance the particulate glucan was reformed.

3. SUMMARY OF THE INVENTION

During an exhaustive investigation of methods by which the triple-stranded helices of glucan might be "relaxed" sufficiently to permit reaction of each of the chains, it was found that when particulate glucan was dissolved in a highly polar solvent (such as DMSO) in the presence of a strong chaotropic agent (such as urea), the glucan is sufficiently structurally disrupted to allow phosphorylation of each of the single chains (or strands) such that the resultant phosphorylated glucan shows the substantially complete absence of the characteristic triple helical structure of particulate glucan. Removal of the resultant phosphorylated glucan shows it to be soluble in water, non-toxic, non-immunogenic, substantially nonpyrogenic and capable of exerting profound immunobiological responses when administered in vivo to animals and humans.

Based on these discoveries, the invention provides a new class of soluble phosphorylated glucans (a) in which the poly-[beta-(1-3) glucopryanose]chains are phosphorylated in varying degrees; (b) which are non-toxic, non-immunogenic, substantially non-pyrogenic, and (c) which are capable of exerting pronounced immunobiological responses when administered in vivo in animals and humans. These new soluble phosphorylated glucans, which are further characterized by a substantial absence of the triple helical structure of particulate glucans, immunostimulate macrophage activity with resulting activation of other immunoactive cells in the reticuloendothelial and immune systems. Additionally these soluble phosphorylated glucans enhance hemopoietic activity including but not limited to leukopoiesis. These soluble phosphorylated glucans exhibit cytostatic effects against adenocarcinomas and sarcomas in vivo, and against lymphocytic leukemia cells in vitro. Not only do these soluble phosphorylated glucans stimulate macrophage cells in vivo, but they exert profound stimulatory effects on macrophage cells cultured in vitro. Such immunostimulation of macrophage cells is invariably accompanied by production of a macrophage cytotoxic/cytostatic factor (MCF), protein or proteins of unknown structure, which are selectively toxic to cancers cells, particularly adenocarcinomas.

Additionally, the invention provides a process for producing these soluble phosphorylated glucans by dissolving a particulate glucan (preferably prepared from *Saccharomyces cerevisiae* although other microbial sources may be used) in a highly polar solvent which contains a strong chaotropic agent, and reacting the resultant glucan with phosphoric acid to form a soluble phosphorylated glucan, and recovering the resultant phosphorylated glucans from the reaction mixture.

The immunobiological properties of the soluble phosphorylated glucans of the invention include (1) the ability to prevent mortality due to overwhelming gram negative bacterial infections; (2) the ability to prevent mortality due to gram positive bacterial infections; (3) the ability to modify mortality from spontaneous infections in profoundly immuno-suppressed animals and man; (4) the ability to modify enhanced susceptibility of immunosuppressed animals and man to gram negative bacterial infections; (5) the ability to significantly modify viral infections; (6) the ability to modify spontaneous infections induced by fungal and other parasitic microorganisms; (7) the ability t significantly inhibit primary tumor growth when used alone and to exert a synergistic effect against primary tumor growth when used in combination with anti-cancer agents; (8) the ability to act synergistically with anti-cancer agents in the regression of primary malignant lesions as well as metastatic lesions in animals and man; and (9) the ability to increase the tensile strength of wounds.

Because of these unique properties, the soluble phosphorylated glucan is particularly useful for promoting wound healing or repair. Thus, the present invention provides compositions and methods for the promotion of wound healing which comprise administering to an animal or a human an effective amount of soluble phosphorylated glucan either alone or in combination with a physiologically acceptable carrier. The compositions and methods of the present invention are particularly useful for the promotion of healing of wounds of various etiologies including, but not limited to: surgical wounds; pressure wounds, such as decubitus ulcers, etc.; trauma wounds; malignant lesions or ulcerations; burn wounds; diabetic ulcers; venous stasis ulcers; etc.

Because the present compositions are soluble in water or aqueous solutions, are non-toxic non-immunogenic and non-pyrogenic they are advantageously administered by a variety of systemic routes including orally, by injection including but not limited to intravenously, intraperitoneally, subcutaneously, intramuscularly, intradermally, etc., as well as by topical application as a dry powder or in a suitable physiologic carrier, by topical application to nasal and nasopharyngeal linings, and by inhalation via aerosolization and application to respiratory tract linings, etc.

4. BRIEF DESCRIPTION OF THE FIGURES

The present invention may be more fully understood by reference to the following detailed description of the invention, examples of specific embodiments and the appended figures in which:

FIG. 1 is a representation of the nuclear magnetic resonance spectrum of soluble phosphorylated glucan at 27 mg/ml.

FIGS. 2A and 2B are representation of the nuclear magnetic resonance spectrum of a commercially available preparation of lentinan (Ajinomoto co. Inc., Tokyo, Japan). FIG. 2A is an illustration of the spectrum obtained at a concentration of 40 mg/ml. FIG. 2B is an illustration of the spectrum obtained at a concentration of 3 mg/ml lentinan.

5. DETAILED DESCRIPTION OF THE INVENTION

Aqueous soluble phosphorylated glucan represents a novel class of soluble phosphorylated glucans in which poly-[beta-(1-3)glucopyranose] chains are phosphorylated in varying degrees. Soluble phosphorylated glucan shows the substantially complete absence of the characteristic triple helical structure of particulate glucan. Because soluble phosphorylated glucan enhances the tensile strength of wounds as well as stimulating macrophage cell proliferation and phagocytic activity, it is advantageously used to enhance the process of healing or repair of wounds induced by a variety of etiologies including but not limited to surgical wounds; pressure wounds, such as decubitus ulcers, etc.; trauma wounds; malignant lesions or ulcers; burn wounds; diabetic ulcers; venous stasis ulcers; etc. Soluble phosphorylated glucan is also efficacious against infections induced by bacteria, fungi, viruses and parasites. Hence the infectability of these agents in wounds may be advantageously modified by the compositions and methods of the invention. Moreover, soluble phosphorylated glucan is also directly cytostatic/cytotoxic against specific malignant tumor cells such as melanoma cells, lymphocytic leukemia cells, sarcoma cells, etc. Hence the present compositions and methods may be particularly advantageous for use in promoting healing of lesions or ulcers associated with such malignancies.

Because of the potent activity of soluble phosphorylated glucan in stimulating the immune response and reticuloendothelial system, it is particularly useful for prophylactic and therapeutic applications against a variety of diseases induced by bacteria, viruses, fungi, and parasitic organisms. Copending application of Williams, Browder and DiLuzio, Ser. No. 13,082, filed on even date herewith is directed specifically to compositions and methods for these applications and is incorporated herein by reference.

Because of the potent cytostatic/cytotoxic effects of soluble phosphorylated glucan against melanomas, sarcomas and lymphocytic leukemias, and the ability to induce production of a macrophage cytotoxic/cytostatic factor (MCF) which is selectively toxic to cancer cells, particularly adenocarcinoma, as well as the profound stimulation of hemopoietic activity and macrophages, it is particularly useful for therapeutic applications against a variety of neoplastic diseases. Copending application of Williams, Browder and DiLuzio, Ser. No. 13,298, filed on even date herewith is directed specifically to compositions and methods for these applications and is incorporated herein by reference.

5.1. PROCESS FOR PREPARATION OF SOLUBLE PHOSPHORYLATED GLUCAN

Aqueous soluble phosphorylated glucan is prepared by a process which results in a unique class of products different from any other glucans previously described.

Soluble phosphorylated glucan is prepared from particulate glucan, a neutral polyglucose derived, for example from *Saccharomyces cerevisiae*, as follows: particulate glucan is suspended in a solution of a strong chaotropic agent in an aprotic solvent such as dimethylsulfoxide (DMSO) with constant stirring. The strong chaotropic agent "relaxes" hydrogen bonding along the polyglucose chain, thus unfolding the molecule. It is preferred to use a fairly high concentration of a strong chaotropic agent such as urea ranging from about 4–12M to prevent reformation of hydrogen bonds. The mixture is then heated and maintained at about 50°–150° C. and phosphoric acid is slowly added with constant stirring. A precipitate comprising the soluble phosphorylated glucan product is apparent after about 1 hour. It is preferred to maintain the reaction mixture at about 100° C. for about 3–12 hours to increase the yield of bioactive product. In practice, after reaction for about 6 hours at about 100° C., the yield is approximately 70–90%. The degree of phosphorylation of the soluble product varies slightly with reaction time (e.g., 1.48% for 3 hours; 2.23% for 6 hours).

The bioactive soluble phosphorylated glucan product is isolated from the reaction mixture as follows: the mixture is cooled to stop the phosphorylation reaction and diluted with a volume of distilled water sufficient to resuspend the precipitate. The resulting solution is filtered through coarse, medium and fine sintered funnels to remove any remaining precipitate. The solution is then molecularly sieved to remove all components of less than about 10,000 daltons molecular weight (MW). Thus, DMSO, urea, glucose and any unreacted phosphoric acid are removed from the solution. Molecular sieving may be accomplished by any method that removes these low (i.e., less than about 10,000 daltons) MW components. In one illustrative example, the solution is sieved using Spectrapor membrane dialysis tubing and dialyzing against running distilled water for about 5 days. In another illustrative example, the solution is sieved using a Millipore dialyzer/concentrator with a 10,000 dalton MW membrane filter and a large volume of dialyzing solution. Following molecular sieving, the resulting solution is concentrated and lyophilized to yield the final soluble phosphorylated glucan in the form of a fluffy powder composition. Crystalline structures are not observed.

The particulate glucan used in the process for preparing the soluble phosphorylated glucan according to the present invention may be isolated from the cell wall of *S. cerevisiae* by known methods (see e.g., Di Luzio et al., 1979, Internat'l J. Cancer 24: 773–779; Hassid et al., 1941, J. Amer. Chem. Soc. 63: 295–298 incorporated herein by reference). Briefly, in practice the particulate glucan is prepared as follows: dry yeast is digested in aqueous sodium hydroxide solution and heated to about 100° C. for about 4 hours, then allowed to settle overnight. The supernatant is decanted and the procedure is repeated three times. The residue is acidified using hydrochloric acid, heated to and maintained at 100° C. for about 4 hours, and cooled overnight. The supernatant is decanted and the acid digestion is repeated twice. The residue is then washed repeatedly with distilled water and extracted with ethanol for at least 24 hours. The reddish-brown supernatant is then aspirated and discarded. The ethanol extraction is repeated until the supernatant is essentially colorless. The ethanol is removed by repeatedly washing the residue with distilled water. The particulate glucan is collected by centrifugation or filtration.

A variety of compounds, other than urea, known to function as "molecular relaxants" were also evaluated to prevent reformation of hydrogen bonds after DMSO had been used to "relax" the triple helical configuration of particulate glucan. These include (1) ethylene diamine tetracetic acid; (2) hydrazine sulfate; (3) monoethanol amine; (4) guanidine; (5) guanine, and (6) thiourea. Additionally, surfactants and emulsifying agents such as Tween-20 and phospholipid emulsifying agents such as Alcolec and Centrolex f (lecithin) were also employed in an attempt to solubilize and phoshorylate particulate glucan. In no case was a soluble immunobiologically active preparation obtained.

Additionally, soluble phosphorylated glucan can be prepared from neutral polyglucose or polyglucose-protein products derived from a variety of other microbial sources. A non-exhaustive list of such sources is presented in Table 1.

TABLE 1
EXAMPLES OF SOURCES OF GLUCAN WHICH CAN BE EMPLOYED FOR THE PREPARATION OF SOLUBLE PHOSPHORYLATED GLUCAN

*Alcaligenes faecalis*
*Auricularia auricula-judae*
*Auricularia polytricha*
*Candida utilis*
*Cladosporium fulvum*
*Claviceps purpurea*
*Cochliobolus sativus*
*Coriolus versicolor*
*Corinellus shiitake*
*Corticium vagum*

TABLE 1-continued
EXAMPLES OF SOURCES OF GLUCAN WHICH CAN BE EMPLOYED FOR THE PREPARATION OF SOLUBLE PHOSPHORYLATED GLUCAN

*Grifola umbellata*
*Lentinus edodes*
*Pichia fermentans*
*Poria cocos*
*Saccharomyces cerevisiae*
*Sclerotium coffeicolum*
*Sclerotium delphnii*
*Sclerotium glucanium*
*Sclerotium rolsfi*
*Shizophyllum commune*
*Streptococcus salvarius*
*Stereum sanguinolentum*
*Wingea robertsii*

According to another alternate embodiment of the present invention, the soluble phosphorylated glucan may be obtained from the medium used to culture an organism such as *Sclerotium glucanium* using a novel, rapid process. Briefly in practice, a colloidal glucan is prepared from *Sclerotium glucanium* as follows:

A crude sclero-glucan, comprising a polyglucose chain of linearly arranged glucose units linked by beta 1-3 glucosidic bonds in which about 30-35% of the linear chains have a single glucose unit attached via a beta 1-6 bond obtained from the medium used to culture *Sclerotium glucanium*, is mixed slowly with aqueous sodium hydroxide solution with heat and constant stirring. The mixture is allowed to stand at room temperature for about 4 days, heated to about 50°-100° C. for about 15-60 minutes and then the mixture is allowed to cool to room temperature.

The colloidal glucan is isolated from the mixture either by centrifugation or filtration. To illustrate, when filtration is used a series of filters of decreasing pore size such as 3.0, 1.2, 0.8, 0.65 microns are used. The resulting dark amber filtrate is diluted with water and molecularly sieved to removed all components of less than about 10,000 daltons molecular weight. In one illustrative example, the mixture is sieved using spectrapor membrane dialysis tubing and dialyzing against 40 liters of water. The final concentrated mixture having about neutral pH is lyophilized yielding an amber spongy glucan material. In another illustrative example, the mixture is dialyzed and concentrated using a Pellicon dialyzing unit. The mixture is dialyzed against 75 liters of pure water. The final concentrated mixture having about neutral pH is lyophilized yielding an amber spongy colloidal glucan material.

Soluble phosphorylated glucan is prepared from the colloidal glucan as described above. Briefly, colloidal glucan is suspended in a solution of a strong chaotropic agent in an aprotic solvent such as dimethylsulfoxide (DMSO) with constant stirring. The strong chaotropic agent "relaxes" hydrogen bonding along the polyglucose chain, thus unfolding the molecule. It is preferred to use a fairly high concentration of a strong chaotropic agent such as urea ranging from about 4-12M to prevent reformation of hydrogen bonds. The mixture is then heated and maintained at about 50°-150° C. and phosphoric acid is slowly added with constant stirring. A precipitate comprising the soluble phosphorylated glucan product is apparent after about 1 hour. It is preferred to maintain the reaction mixture at about 100° C. for about 3-12 hours to increase the yield of bioactive product. In practice, after reaction for about 6 hours at about 100° C., the yield is approximately 70-90%. The degree of phosphorylation of the soluble product varies lightly with reaction time (e.g., 1.48% for 3 hours; 2.23% for 6 hours).

5.2. CHARACTERIZATION OF SOLUBLE PHOSPHORYLATED GLUCAN

The solubility of the soluble phosphorylated glucan obtained from *S. cerevisiae* prepared according to the present invention is greater than about 50 mg/ml in water. Aqueous solutions of the soluble phosphorylated glucan are non-viscous and do not taste sweet.

5.2.1. ELEMENTAL COMPOSITION

The elemental composition of the soluble glucan preparation, determined by Galbraith Laboratories, (Knoxville, Tenn.) is illustrated in Table 2. The data presented in Table 2 permits the average empirical formula of this preparation to be written as follows:

$C_{40}H_{87}PO_{37}$.

Thus, there is an average of one phosphate group for every 6.6 glucose residues in the soluble phosphorylated glucan.

TABLE 2
ELEMENTAL COMPOSITION OF SOLUBLE PHOSPHORYLATED GLUCAN[a]

| Element or Component | Mole % |
| --- | --- |
| Carbon | 34.66 |
| Hydrogen | 6.29 |
| Oxygen | 42.83 |
| Nitrogen | 0.64 |
| Sulfur | 0.11 |
| Phosphorus | 2.23 |
| Water of Hydration | 11.78 |

[a]Determined after 6 hours phosphorylation.

5.2.2. STRUCTURAL CONFIGURATION

A number of methods were utilized to determine the molecular weight (MW) and various features of the structural configuration of the soluble phosphorylated glucan.

5.2.2.1. MOLECULAR SIEVING

Column chromatograph using Sepharose CL-6B-200 (Pharmacia Fine Chemicals, Piscataway, N.J.) indicated that 80% of the soluble glucan has a MW range from 10,000 to 100,000 daltons, while 20% has a MW range from about 100,000 to about 500,000 daltons.

5.2 2.2. NUCLEAR MAGNETIC RESONANCE SPECTROSCOPY

Carbon-13 nuclear magnetic resonance ($^{13}$C-NMR) spectroscopy using a Brucker WP-200 spectrometer (Brucker Instruments, Billerica, Mass.) was performed to determine several structural properties of the soluble phosphorylated glucan from *S. cervisiae* prepared according to the present invention.

The samples for NMR studies were prepared using a 10% deuterium oxide (D$_2$O) in water. Samples were first run with no reference material, and then after the addition of a small aliquot of 1,4-dioxane. All samples were placed in 10 mm diameter tubes.

The $^{13}$C-NMR spectral study of soluble phosphorylated glucan indicated a beta-1-3 glucan structure with no branching at the C-6 carbon (see FIG. 1). The NMR spectrum indicates a substantial absence of the triple helical structure of particulate glucans. The degree of phosphorylation was estimated to be 3.6% which is in essential accord with analytical data.

In contrast to the spectra of soluble phosphorylated glucan from *S. cerevisiae* prepared according to the present invention, a lentinan preparation (Ajinomoto Co. Inc., Tokyo Japan), a branched beta-1-3 and 1-6 D glucan, at either 40 mg/ml (FIG. 2A) or 3 mg/ml (FIG. 2B) demonstrated attenuation of the NMR spectra. This is presumed to be due to the gel state of this molecule, particularly at 40 mg/ml concentration. No signals were obtained in a 10% $D_2O$ solution in the non-gel 3 mg/ml concentration.

Comparison of FIG. 1 with FIG. 2 demonstrates complete structural and conformational differences between lentinan and soluble phosphorylated glucan. In contrast to the disordered conformation of lentinan at the beta-1-6 linkages (Saito et al., 1977, Carbohydrate Research, 58: 293-305) ordered conformation of soluble phosphorylated glucan according to the present invention is manifested.

5.3. NON-TOXICITY, NON-PYROGENICITY NON-IMMUNOGENICITY OF SOLUBLE PHOSPHORYLATED GLUCAN

Since the soluble phosphorylated glucan offers important advantages over particulate glucan as an injectable biological response modulator, characteristic toxicity, pyrogenicity and immunogenicity of the soluble glucan are described below with particular reference to comparison of these properties of particulate glucan.

5.3.1 NON-TOXICITY

Acute toxicity was evaluated following a single intravenous injection of soluble phosphorylated glucan at a variety of doses into normal animals. Treated animals were observed for 30 days post-injection.

In one series of experiments, 49 ICR/HSD mice were divided into 3 groups of 15 mice each and 2 groups of 2 mice each. Groups 1-3 received 0.5 ml saline solution containing soluble phosphorylated glucan at respectively 40, 200 and 1000 mg/kg; Groups 4 and 5, 1600 and 2000 mg/kg. No mortality was observed in any group. Moreover, no physiological or behavioral alterations were apparent. In marked contrast, in mice treated similarly with particulate glucan, 20% mortality was observed at 250 mg/kg and 100% mortality at 500 mg/kg.

In another series of experiments, two groups of 5 Sprague Dawley rats each were treated with soluble phosphorylated glucan at respectively 250 and 500 mg/kg via intravenous injection. No mortality or alteration of physiological or behavioral functions was apparent in either group. In contrast, 30% and 100% mortality were observed following intravenous injection of particulate glucan at 75 and 150 mg/kg respectively.

Chronic toxicity was evaluated following twice weekly intravenous injections of saline solution containing soluble phosphorylated glucan at 0, 40, 200 and 1000 mg/kg doses. Body and organ weights, gross and microscopic pathology, serum electrolytes, solutes and serum enzymes indicative of renal and hepatic function were monitored.

In one series of experiments mice were weighed respectively at 0, 8, 11, 15, 22 and 30 days post-treatment with soluble phosphorylated glucan. No significant difference was observed in body weight at any dose of soluble phosphorylated glucan administered. After 30 days chronic treatment, animals were sacrificed. No change was seen in weight of liver, lung and kidney. A statistically significant increase in spleen weight was note in mice treated with 40 and 100 mg/kg soluble glucan ($0.01 < p < 0.001$), but not in mice treated with 200 mg/kg.

In another series of experiments, mice were weighed respectively at 0, 15, 30, 49 and 60 days post-phosphorylateglucan treatment (twice weekly) with soluble No significant difference was observed in body weight at any dose of soluble phosphorylated glucan administered. After 60 days chronic treatment with soluble phosphoryated glucan, animals were sacrificed. No significant difference was observed in weight of the liver, kidney or lung. A statistically significant increase in spleen weight was apparent in mice treated with 1000 mg/kg soluble phosphorylated glucan ($p < 0.001$).

After 30 or 60 days chronic treatment, no significant alteration was apparent in the following serum components: glucose, blood urea nitrogen (BUN), uric acid, cholesterol, triglyceridss, total protein, albumin, globulin, creatinine, calcium, phosphorous, sodium, potassium, chloride, bicarbonate and anion gap. Moreover, no significant alteration was apparent in the following enzymes: alkaline phosphatase, lactic dehydrogenase, serum glutamic oxalacetic transaminase, serum glutamic pyruvic transaminase and creatinine phosphokinase. No change was detectable in serum bilirubin.

Histological studies on tissues obtained from mice following 30 days chronic treatment showed essentially normal liver histology in mice receiving 40 and 200 mg/kg soluble phosphorylated glucan per injection. In animals receiving 1000 mg/kg soluble phosphorylated glucan, monocytic infiltrates were readily apparent in the liver. Lung and kidney tissues were essentially normal in all mice.

Histological studies on tissues obtained from mice following 60 days chronic treatment showed few hepatic granuloma of an isolated nature in animals receiving injections at 40 and 200 mg/kg doses. A higher number of monocytic infiltrates was observed in mice receiving injections at 1000 mg/kg. In all autopsied animals, lung tissue was essentially normal.

Chronic toxicity was further evaluated using guinea pigs (Harlan Sprague Dawley, Houston, Tex.) receiving 5 ml intraperitoneal injections of saline solution containing soluble phosphorylated glucan at 250 mg/kg for 7 days (FDA required test). Results presented in Table 3 indicate that there was an impairment of growth of guinea pigs receiving soluble glucan treatment when compared to controls receiving an equivalent volume of 0.9% saline solution. Following 7 days chronic treatment, body weight of treated animals was however, significantly increased by 9% as compared to initial weight.

TABLE 3
EFFECT OF CHRONIC ADMINISTRATION OF SOLUBLE PHOSPHORYLATED GLUCAN ON BODY WEIGHT

| Treatment | Mean Body Weight (gm)[a] Days | | | | | | |
|---|---|---|---|---|---|---|---|
| | 1 | 2 | 3 | 4 | 5 | 6 | 7 |
| Saline | 213.8 ± 4.0 | 225.2 ± 6.6 | 227.4 ± 7.1 | 234.2 ± 7.3 | 239.7 ± 6.1 | 244.2 ± 5.2 | 253.8 ± 7.5 |
| SPGLN[b] | 208.9 ± 2.9 | 202.3 ± 5.0 | 203.9 ± 5.3 | 207.4 ± 5.3 | 214.3 ± 6.0 | 215.6 ± 6.6 | 227.3* ± 6.6 |

[a] Values represent mean body weight (gm) ± standard error. N = 5 animals.
[b] SPGLN designates soluble phosphorylated glucan.
*$p < 0.01$ Chronic Toxicity was also evaluated in 2 adult female dogs receiving twice weekly intravenous administration (5 mg/kg) of soluble phosphorylated glucan for 120 days. The dogs were fed Purina Chow and water ad libitum supplemented with one can commercial dog food (Alpo ™) twice weekly. Body weight and serum solutes, electrolytes and enzymes were monitored at 0, 17, 24, 38, 80 and 120 days. Following 120 days chronic treatment, a mean weight gain of 2.8 kg or about 22% body weight was observed.

No significant difference was observed in the following serum solutes: glucose, BUN, uric acid, cholesterol, triglycerides, total protein, albumin, globulin, or creatinine. No significant difference was observed in the following serum electrolytes: calcium, phosphorous, sodium, potassium, chloride, bicarbonate, and anion gap. No significant difference was observed in the following serum enzymes: alkaline phosphatase, lactic dehydrogenase, serum glutamic oxalacetic transaminase, serum glutamic pyruvic transaminase and creatinine phosphokinase.

Additionally, no significant difference has been observed in the serum biochemistry of a patient following therapy for 3 months with soluble phosphorylated glucan at 50 mg/ml, administered three times per week.

5.3.2 NON-PYROGENICITY

Pyrogenicity of soluble phosphorylated glucan was evaluated following a single intravenous injection to conscious dogs at doses of 7.5 mg/kg and 30 mg/kg. Body temperature was monitored for 14 days post-injection.

Results presented in Table 4, demonstrate no pyrogenic reaction in this chronic animal model.

TABLE 4
ABSENCE OF AN ACUTE OR CHRONIC PYROGENIC RESPONSE IN DOGS

| Treatment Dose[a] (mg/kg) | Mean Body Temperature (°C.) Time (Hours) | | | | | |
|---|---|---|---|---|---|---|
| | 0 | 1 | 6 | 24 | 144 | 336 |
| 7.5 | 38.3 | 37.4 | 38.3 | 38.3 | 38.3 | 38.4 |
| 30.0 | 38.6 | 37.0 | 38.0 | 38.5 | 38.4 | 38.6 |

[a] N = 3 dogs/group.

Pyrogenicity was also evaluated using three dogs anesthetized with Nembutal (30 mg/kg) receiving multiple injections of increasing doses of 1, 5, 10, 15, 25 and 50 mg/kg of soluble phosphorylated glucan over a three hour period. Body temperature was determined at 15 minutes following bolus injections. No pyrogenic effect was observed at any dose.

Pyrogenicity of soluble phosphorylated glucan was also evaluated in rabbits. Seven rabbits were divided into 2 groups of 2 and 5 rabbits each. Group 1 received an isovolumetric saline solution; Group 2, received 5 mg/kg soluble phosphorylated glucan in saline solution by intravenous injection. Core body temperature was monitored at 15 minute intervals for 100 minutes following a single bolus injection. Control rabbits showed a mild decrease of 0.2° C. in body temperature. Rabbits treated with soluble phosphorylated glucan showed a mean increase of 0.44° C. Thus, there was a slight pyrogenicity seen in rabbits.

5.3.3. NON IMMUNOGENICITY

The interfacial ring test, designed to detect the presence of IgG antibodies, was used to evaluate the immunogenicity of soluble phosphorylated glucan when chronically administered to dogs for 120 days.

Serum samples were obtained from an adult female dog following 120 days chronic treatment with twice weekly intravenous injections of 5 mg/kg sterile, pyrogen-free soluble phosphorylated glucan. The interfacial ring precipitin test was performed as follows: 0.1 ml of undiluted antisera was pipetted into test tubes. The antigen or phosphorylated soluble glucan at dilutions of 1:2, 1:4, 1:8,.1:16 and 1:32 was layered onto the anti-sera to form a straight interface. Formation of a white precipitin ring at the interface, indicates that presence of antibody specific for the glucan. No precipitin ring was detected at any antigen dilution.

5.4. APPLICATIONS FOR WOUND HEALING

Because of the demonstrated ability of soluble phosphorylated glucan to enhance the tensile strength of wounds, (see Section 7, infra) and the profound activity of soluble phosphorylated glucan in stimulating macrophage cell number, phagocytic activity and interaction of macrophages, it is advantageously useful for promoting the wound healing process. According to the present invention, soluble phosphorylated glucan is used to promote healing of a variety of types of wounds including, but not limited to surgical wounds; trauma wounds; pressure wounds such as decubitus ulcers, etc.; malignant lesions or ulcers; burn wounds; diabetic ulcers; venous stasis ulcers; etc.

In addition to its profound immunobiological activities, soluble phosphorylated glucan possesses a number of characteristics which make it particularly advantageous for the promotion of wound healing, including, but not limited to the following:

(1) Soluble phosphorylated glucan is soluble in water or aqueous solutions;
(2) Soluble phosphorylated glucan has very low toxicity; and
(3) Soluble phosphorylated glucan is not associated with adverse side effects associated with particulate glucan (see Section 2.2, supra) when administered systemically to animals or man.

Because of the ability of soluble phosphorylated glucan to exert a synergistic effect on infections induced by bacteria, viruses, fungi and parasitic organisms when administered in combination with an antimicrobial agent, according to another embodiment of the present invention, soluble phosphorylated glucan is advantageously used in combination with an antimicrobial agent to promote healing of wounds including, but not limited to, surgical wounds, trauma wounds, pressure wounds, burn wounds, etc. Examples of antimicrobial agents that may be used according to this embodiment include those listed in Table 5. Table 5 is in no way meant to be an exhaustive list. Also a combination of one or more antimicrobial agents may be used together with soluble phosphorylated glucan to promote wound healing.

TABLE 5
EXAMPLES OF ANTIMICROBIAL AGENTS

I. ANTIBACTERIALS
Aminoglycosides
Streptomycin
Neomycin
Kanamycin
Amikacin
Gentamicin
Tobramycin
Streptomycin B
Dihydrostreptomycin
Spectinomycin
Penicillin
Ampicillin
Hetacillin
Amoxicillin
Carbenicillin
Cephalosporins
Cephaloridine
Cephalothin sodium
Cephaloglycin dihydrate
Cephalexin monohydrate
Tetracycline
Tetracycline hydrochloride
Oxytetracycline hydrochloride
Chlorotetracycline hydrochloride
Doxocycline monohydrate
Methacydine hydrochloride
7-Chloro-6-dimethyltetracycline
Erythamycin
Sulfonamides
Carbomycin
Oleanodmycin
Troleandomycin
Polymixin B collistin
Chloramphenicol II. ANTIFUNGALS
Amphotericin B
Flucytosine
Nystatin
Grisiofulvin
Sulfamerizane
Thimerosal
Tolnaftate III. ANTIVIRALS
Acyclovir
3'-azido-3'-deoxythmyidine
Vira A
Symmetrel
Idoxuridine
Bromovinyldeoxuridine
(S)—9-(3-Hydroxy-2 phosphonyl methoxypropyl) adenine IV. ANTIPARASITICS
Sulfonamides
Pyrimethamine
Clindamycin Because of the ability of soluble phosphorylated glucan to exert a synergistic effect against various neoplasias when administered in combination with an anti-tumor or anti-cancer agent, according to yet another embodiment of the present invention, soluble phosphorylated glucan is advantageously used in combination with an anti-tumor or anti-cancer agent to promote healing of malignant lesions or ulcerations. Table 6 is a non-exhaustive list of anti-tumor or anti-cancer agents that may be used according to this embodiment.

TABLE 6
EXAMPLES OF ANTI-TUMOR AGENTS WHICH MAY BE COMBINED WITH SOLUBLE PHOSPHORYLATED GLUCAN FOR TREATMENT OF NEOPLASIAS

I. ALKYLATING AGENTS
CLASSIC ALKYLATING AGENTS
Bis (chloroethyl) amines
Asaley
Chlorambucil
Cyclophosphamide (CTX)
Ifosfamide
Mechlorethamine ($HN_2$)
Melphalan (1-PAM)
Uracil mustard
Ethyleneimines
Triethylene thiophosphoramide (Thio-TEPA)
Alkyl sulfonates
Busulfan
Yoshi 864
NITROSOUREAS
Carmustine (BCNU)
Estramustine
Lomustine (CCNU)
Semustine (Me-CCNU)
Streptozocin
Chlorozotocin
ANTITUMOR ANTIBIOTICS
Anthracyclines
Doxorubicin
Daunorubicin (Adriamycin)
Rubidazone
Carminomycin
Aclacinomycin
Chromomycin $A_3$
Dactinomycin
Mithramycin
Mitomycin C
Piperazinedione
Bleomycins
4'-Epiadriamycin
4'-Deoxyadriamycin
Neocarzinostatin
Bisantrene
2'-Deoxycoformycin
Actinomycin
Mitoxantrone
MISCELLANEOUS ALKYLATOR AGENTS
Cisplatin
Decarbazine (DTIC)
Galactitol
Hexamethymelamine
Pipobroman
II. ANTIMETABOLITIES
FOLATE ANTAGONISTS
Ethanesulfonic acid compound (Baker's antifol)
Methotrexate (MTX)
Dichloromethotrexate
Aminopterin
PURINE ANTAGNOSITS
Azathioprine
Mercaptopurine (6-MP)
Thioguanine (6-TG)
5-Azacytidine
Cyclocytidine
III. PLANT ALKALOIDS
Vinblastine
Vincristine
Vindesine
Etoposide (VP-16-213)

TABLE 6-continued
EXAMPLES OF ANTI-TUMOR AGENTS WHICH MAY BE COMBINED WITH SOLUBLE PHOSPHORYLATED GLUCAN FOR TREATMENT OF NEOPLASIAS VM-26 (teniposide)
Maytansine

IV. MISCELLANEOUS AGENTS

Cytembena
Hydroxyurea
Razoxane
Asparaginase
Procarbazine
Cytarabine (ARA-C)
Fluorouracil (5-FU)
Floxuridine (FUDR)
Alpha-difluoromethylornithine
Azaribine

5.5. ROUTES AND METHODS OF ADMINISTRATION

The soluble phosphorylated glucans of the present invention can be administered for wound healing applications by a number of routes, including but not limited to: orally; by injection including but not limited to intradermally, intraveneously, intraperitoneally, subcutaneously, intramuscularly, etc.; topically as a dry powder or in a suitable physiologic carrier; by topical application to nasal and nasopharyngeal linings, and by inhalation via aerosolization and application to respiratory tract linings; etc. When administered to an animal or a human, the soluble phosphorylated glucan may be used as a dry powder or combined with water, an aqueous solution or any physiologically acceptable pharmaceutical carrier or vehicle. Additionally, soluble phosphorylated glucan may be administered in combination with either an antimicrobial agent or an anti-cancer agent. When a combination of soluble phosphorylated glucan and either an antimicrobial agent or an anticancer agent is desired, each agent may be simultaneously administered or soluble phosphorylated glucan may be combined with one or more antimicrobial agents or anti-cancer agents and administered as a single composition. The combination may be administered by any of the routes described above herein.

According to other embodiments of the present invention, the soluble phosphorylated glucan or pharmaceutical composition may be administered by a number of delivery modalities including but not limited to the following: incorporated into liposome vesicles; in combination with an albumin complex to increase the intravascular half-life, in combination with a targeting agent such as a polyclonal or monoclonal antibody against an antigen associated with a specific neoplasia etc.; in combination with an anhydrous lipid base for topical or parental administration, etc. In addition, the soluble phosphorylated glucan, either alone or in combination with a known antibiotic or antitumor agent can be impregnated on bandages, sutures or dressings either as a dry powder or in a suitable physiologic carrier.

The following series of Examples are presented for purposes of illustration and not by way of limitation on the scope of the invention.

6. PREPARATION OF SOLUBLE PHOSPHORYLATED GLUCANS

6.1. PREPARATION FROM PARTICULATE GLUCAN OBTAINED FROM SACCHAROMYCES

Particulate glucan was prepared from *Saccharomyces cerevisiae* according to the method of Di Luzio et al. (1979, Int'l J. Cancer 24: 773–779). Briefly, using a 6 l flask, 540 gm of dry yeas (Universal Foods Corp., Milwaukee, Wis.) was suspended in 3 l of 3% aqueous sodium hydroxide solution. The suspension was placed in boiling water bath 4 hours, cooled overnight and the supernatant decanted. This procedure was repeated three times. The residue was then acidified with 800 ml of concentrated hydrochloric acid plus 2 l of 3% hydrochloric acid and placed in a boiling water bath for 4 hours. The suspension was allowed to stand overnight and the supernatant decanted. The residue was further digested with 3 l of 3% hydrochloric acid at 100° C. for 4 hours, cooled overnight and decanted. The 3% hydrochloric acid digestion was repeated twice. The residue was then washed three times with distilled water (20° C.) and twice with distilled water at 100° C. One l of ethyl alcohol was added to the residue, mixed thoroughly and allowed to stand a minimum of 24 hours for maximum extraction. The dark reddish-brown alcohol supernatant was aspirated from the residue and discarded. The alcohol extraction procedure was repeated until the alcohol supernatant was essentially colorless. The alcohol was removed by washing the residue four times with hot water; the particulate glucan preparation was then collected by centrifugation, frozen and lyophlized.

Soluble phosphorylated glucan was prepared according to the method described in Section 5 by solubilization and phosphorylation of the particulate glucan as follows:

18 gm of urea (6M) was dissolved in a flask containing 50 ml dimethylsulfoxide (DMSO) with constant stirring. One gm of particulate glucan was added to form a finely divided suspension. The flask was heated to 100° C. and 10 ml of phosphoric acid (85%) was added slowly dropwise. The mixture was maintained at 100° C. for 3–12 hours by immersion in a boiling water bath. It is preferred to allow the reaction to proceed for about 6 hours.

During the heating process, a precipitate was formed which became visible after about 1 hour and increased in amount thereafter. After about 6 hours, the mixture was cooled and diluted with 200 ml distilled water to resuspend the precipitate. The mixture was then filtered through coarse, medium and fine sintered funnels to remove the precipitate.

The resulting solution was then molecularly sieved in order to remove low molecular weight (MW) fractions including glucose, DMSO and urea.

In one series of experiments, molecular sieving was accomplished by dialysis for 5 days against running distilled water using Spectrapor membrane dialysis tubing (Fisher Scientific Co; Pittsburgh, Penn). The MW size range of pores of this tubing is about 12,000 daltons. In another series of experiments, molecular sieving was accomplished using a Millipore dialyzer/concentrator (Millipore Corp., Bedford, Mass.) with a 10,000 MW membrane filter. About 70 l of dialyzing solution were used to remove low MW compounds. In either case, tests for the presence of glucose in the final preparation were negative. Moreover, using high performance gas-liquid chromatography, no DMSO was detectable in the final preparation.

Following molecular sieving, the solution containing the phosphorylated soluble glucan was concentrated and lyophilized. This phosphorylated glucan is stable in a lyophilized state for at least 2 years and at least for 15 months in solution maintained at −20° C.

6.2. PREPARATION FROM CORIOLUS VERSICOLOR

Soluble phosphorylated glucan was prepared from a basidiomycete *Coriolus versicolor* (Fr. Quel.) as follows:

A commercially available polysaccharide-protein preparation termed "Krestin" or "PSK" obtained from Sanyko Corporation, Tokyo, Japan, was used as the starting material for the preparation of soluble phosphorylated glucan from *C. versicolor*. This commercial preparation of a relatively crude preparation comprising a beta-1,4, beta-1,3, beta-1,6,-glucan-protein complex. The principal chemical structure of the polyglucose is a main chain of glucose units linked by 1-4 glucosidic bonds, having attached branch or side chains of glucose units linked by beta-1,3 and beta-1,6 glucosidic bonds. The protein content ranges from 15–38%. (Ehrke et al., 1983, Internat'l J. Immunopharm. 5: 34–42: Yamaura and Azuma, 1982, Adv. Immunopharm. 2: 501–507).

Because the commercially available PSK preparation is relatively crude preparation and has a relatively high protein content, intravenous administration of this material is not possible. It must be administered orally.

The PSK polysaccharide-protein complex from *C. versicolor* was prepared as a soluble phosphorylated glucan (hereinafter "soluble phosphorylated-PSK") as described in Section 5. The isolated soluble phosphorylated-PSK was lyophilized.

6.3. PREPARATION FROM SCLEROTIUM

Soluble phosphorylated glucan was prepared from *Sclerotium glucanium* as follows:

A commercially available sclero-glucan termed "Polytran R" obtained from Jetco Chemicals, Inc. (Corsicana, TX) was used as the starting material. This commercial preparation is a monionic polyglucose of greater than 500,000 daltons MW comprising a linear chain of glucose units linked by beta 1-3 glucosidic bonds in which about 30–35% of the linear chains have appended a single glucose unit linked via a beta 1-6 linkage. When mixed with water or an aqueous solution, Polytran R forms a colloidal suspension that becomes increasingly viscous over a 24 hour period. Because of the formation of such viscous gel, Polytran R is not useful for intravenous administration. A novel, rapid process was used to obtain a colloidal glucan from the sclero-glucan as follows:

One hundred forty grams Polytran R was added to 2.0 liters of 1M NaOH, pH about 14 with constant stirring on a hot plate. The mixture was maintained at room temperature for 4 days. Then the mixture was heated to about 85° C. for about 20 minutes, during which time a dark brown color developed in the mixture. After the mixture was cooled to room temperature, it was filtered through coarse and then medium sintered glass funnels. The filtrate was then passed serially through a series of Millipore filters: 3.0, 1.2, 0.8 and 0.65 microns. The resulting clear filtrate had a dark amber color. An aliquot (500 ml) was diluted to 6.0 liters in a dialyzing flask and dialyzed against 40 liters of ultrapure water. The pH of the final concentrated mixture was about 6.7. The colloidal glucan isolated, a light brown spongy material, was lyophilized.

Soluble phosphorylated glucan was prepared from the colloidal glucan as described in Section 5.

In practice, 72 gm of urea (6M) was dissolved in a flask containing 200 ml DMSO with constant stirring. Four gm of colloidal glucan was added to form a finely divided suspension. The flask was heated to 100° C. and 40 ml of phosphoric acid (85%) was added slowly drop wise. The mixture was maintained at 100° C. for 6.0 hours.

During the heating process, a precipitate was formed which became visible and quite noticeable after about 3 hours and increased in amount thereafter. After about 6 hours, the mixture was cooled, and diluted with 4 liters distilled water to resuspend the precipitate. The mixture was then filtered through a 3.0 micron filter.

The resulting solution was molecularly sieved in order to remove low molecular weight fractions. In one series of experiments molecular sieving was accomplished by dialysis (1 liter: 5 liters water).

Following molecular sieving, the solution containing the soluble phosphorylate glucan was concentrated and lyophilized to yield about 4 gms soluble phosphorylated glucan.

PROMOTION OF HEALING SURGICAL WOUNDS

7.1. Topical Administration of Soluble Phosphorylated Glucan

The following example demonstrates that topical administration of soluble phosphorylated glucan is effective in enhancing the healing process of surgical wounds.

Fifty six Sprague-Dawley rats were divided into eight groups of seven each. Surgical incisions (2.0 cm) were made in the dorsal surface of the skin of all animals. The control groups, Group 1 and 5 were untreated; Groups 2 and 6, and 7 and 4 and 8 received respectively 20 mg of soluble phosphorylated glucan obtained from *Saccharomyces cerevisiae* (as described in Section 6.1); soluble phosphorylated glucan obtained from *Scelerotium glucanium* (as described in Section 6.3); and particulate glucan (as described by DiLuzio et al., 1979, Internat'l J. Cancer 24:773–779). All treatments were topically administered directly to the wound site on day. On day 4 animals in Groups 1–4 and on day 7 animals in Groups 5–8 were sacrificed using ether. The tensile strength, i.e., the tension (gm) required to break the wound, was determined using a Constant Speed Tensiometer (W.C. Dillon & Co., Inc., Van Nuys, Calif.). The skin surrounding the wound was excised leaving about 1½ inches of skin on either side of the wound. The skin flaps on either side of the wound were then secured in the tensiometer. Results are illustrated in Tables 7 and 8.

TABLE 7

EFFECT OF TOPICALLY ADMINISTERED GLUCANS ON WOUND HEALING: EVALUATED ON DAY 4 FOLLOWING SURGICAL INCISION

| | Tensile Strength (gm)[a] | | |
|---|---|---|---|
| Control | Soluble Phosphorylated Glucan[b] | Soluble Phosphorylated Glucan-RF[c] | Particulate Glucan |
| 18 | 45 | 73 | 73 |
| 18 | 45 | 50 | 54 |
| 18 | 73 | 50 | 45 |
| 14 | 45 | 45 | 77 |
| 27 | 59 | 86 | 82 |
| 23 | 73 | 86 | 73 |
| 27 | 78 | 91 | 73 |
| x̄: 20.7 ± 1.9 | 59.7 ± 5.6* | 68.7 ± 7.5* | 68.1 ± 5.1* |

[a]Tensile strength refers to the tension required to break the wound (gm). Tensile strength was determined using a Constant Speed Tensiometer (W. C. Dillion & Co., Inc., Van Nuys, CA). x̄: represents mean ± standard error. N = 7/group.
[b]Soluble phosphorylated glucan obtained from *Saccharomyces cerevisiae*.
[c]Soluble phosphorylated glucan obtained from *Sclerotium glucanium* as described in Section 6.3.
*$p < 0.001$.

TABLE 8

EFFECT OF TOPICALLY ADMINISTERED GLUCANS ON WOUND HEALING: EVALUATED ON DAY 7 FOLLOWING SURGICAL INCISION

| | Tensile Strength (gm)[a] | | |
|---|---|---|---|
| Control | Soluble Phosphorylated Glucan | Soluble Phosphorylated Glucan - RF | Particulate Glucan |
| 45 | 45 | 68 | 73 |
| 54 | 45 | 54 | 45 |
| 36 | 45 | 68 | 100 |
| 36 | 45 | 64 | 114 |
| 50 | 100 | 91 | 123 |
| 54 | 109 | 95 | 68 |
| 82 | 104 | 100 | 132 |
| x̄: 51.0 ± 5.9 | 70.4 ± 12.0 | 77.1 ± 6.7* | 93.6 ± 12.2** |

[a]Tensile strength refers to the tension required to break the wound (gm). Tensile strength was determined using a Constant Speed Tensiometer (W. C. Dillion & Co., Inc., Van Nuys, CA). x̄: represents mean ± standard error. N = 7/group.
[b]Soluble phosphorylated glucan obtained from *Saccharomyces cerevisiae*.
[c]Soluble phosphorylated glucan-RF represents soluble phosphorylated glucan obtained from *Scelerotium glucanium* as described in Section 6.3.
*$p < 0.02$.
**$p < 0.01$.

As demonstrated in Tables 7 and 8, topical administration of soluble phosphorylated glucan produced an 188% ($p<0.001$) enhancement in the breaking strength of the wound on day 4, although there was no significant difference observed on day 7 when compared to controls. The soluble phosphorylated glucan derived from Sclerotium (soluble phosphorylated glucan-RF), was also effective in promoting wound repair as denoted by a 231% ($p<0.001$) increase in wound tensile strength on day 4 and 51% ($p<0.02$) enhancement on day 7. These results clearly demonstrate that preparations of phosphorylated glucans are effective in enhancing wound healing.

Additionally, the results presented in Tables 7 and 8 demonstrate that particulate glucan is effective in promoting wound healing as denoted by a 228% ($p<0.001$) enhancement at day 4 and an 84% ($p<0.01$) enhancement at day 7 when compared to controls.

7.2. Systemic Administration of Soluble Phosphorylated Glucan

This example demonstrates that systemic administration of soluble phosphorylated glucan is effective in enhancing healing of surgical wounds.

Forty eight Sprague-Dawley rats were divided into 4 groups of 12 each. A 2.0 cm surgical incision was made through the skin of the dorsal surface of all animals. One day prior to and one day following surgical incisions, Groups 2 and 4 received an intravenous injection of soluble phosphorylated glucan (10 mg/rat). Groups 1 and 3, designated Controls, received an intravenous injection of dextrose (5%). Groups 1 and 2 were sacrificed on day 4, and Groups 3 and 4 on day 7 following the surgical incisions. The tensile strength of skin samples comprising the wound site was determined using a Constant Speed Tensiometer (W. C. Dillon & Co., Inc., Van Nuys, Calif.) as described in Section 7.1. Results are presented in Table 9.

TABLE 9

EFFECT OF SYSTEMIC ADMINISTRATION OF SOLUBLE PHOSPHORYLATED GLUCAN ON WOUND HEALING

| Treatment Groups[a] | Tensile Strength (gm)[b] |
|---|---|
| Day 4 | |
| Control | 9.02 ± 1.84 |
| Soluble Phosphorylated Glucan | 38.2 ± 2.11* |
| Day 7 | |
| Control | 9.07 ± 3.37 |
| Soluble Phosphorylated Glucan | 23.70 ± 3.45** |

[a]Sprague-Dawley rats (250 gm) were injected intravenously with soluble phosphorylated glucan 1 day prior and 1 day following a 2 cm surgical incision through the skin and the dorsal surface. The animals were sacrificed on day 4 and 7 for collection of skin for tensiometry.
[b]Tensile strength refers to the tension required to break the wound (gm). Tensile strength was determined using a Constant Speed Tensiometer (W. C. Dillion & Co., Inc., Van Nuys, CA). The values represent the mean ± standard error. N = 9-13/group.
*$p < 0.001$.
**$p < 0.01$.

As demonstrated in Table 9, systemic administration of soluble phosphorylated glucan produced a 323% ($p<0.000$) enhancement of the tensile strength on day 4 and a 161% ($p<0.01$) enhancement of the tensile strength of the surgical wounds on day 7 compared to controls. Thus, this experiment clearly demonstrates that systemic administration of soluble phosphorylated glucan significantly enhances the wound healing process.

8. ENHANCEMENT OF MACROPHAGE PHAGOCYTIC ACTIVITY

The following experiment demonstrates that administration of soluble phosphorylated glucan significantly enhanced phagocytic function of macrophages.

Twenty male ICR mice were divided into two groups of 10 each. At 3, 2 and 1 day prior to determination of phagocytic activity, Group 1, designated control received injections of isovolumetric saline; Group 2, soluble phosphorylated glucan (200 mg/kg). All injections were administered intravenously.

Phagocytic function was evaluated by measuring the rate of intravascular clearance of colloidal carbon (C11/143 (a), Gunther Wagner, Hanover, Germany) according the method of Wooles et al. (1962, Rad. Res. 16: 546-554). Colloidal carbon was administered (640 mg/kg) intraveneously and serial blood samples were obtained from tail veins. Aliquots were hemolyzed in 4.0 ml of 0.5% sodium carbonate and the concentration of colloidal carbon was determined spectrophotometrically. The half-time (t/2) was taken as the time at which the optical density or concentration was one-half the zero time value as determined by extrapolation of the clearance curves to zero time. Results are presented in Table 10.

TABLE 10
EFFECT OF SOLUBLE PHOSPHORYLATED GLUCAN ON MACROPHAGE PHAGOCYTIC FUNCTION

| Treatment[a] | Body Weight (gm) | Liver Weight (gm) | Intravascular Clearance t/2 (minutes) |
|---|---|---|---|
| Saline | 24.8 ± 0.82 | 1.94 ± 0.05 | 7.6 ± 0.73 |
| Soluble Phosphorylated Glucan | 25.2 ± 1.03 | 1.82 ± 1.03 | 3.5 ± 0.58* |

[a]N = 10 per group.
*p < 0.001

As demonstrated in Table 10, administration of soluble phosphorylated glucan significantly enhanced phagocytic function as reflected by a 55% increase in clearance (Table 10). As previously observed, no increase in liver weight occurred (Table 10).

The invention described and claimed herein is not to be limited in scope by the specific embodiments herein disclosed, since these embodiments are intended as illustrations of several aspects of the invention. Any equivalent embodiments are intended to be this invention. Indeed, various modifications of the invention in addition to those shown and described herein will become apparent to those skilled in the art from the foregoing description. Such modifications are also intended to fall within the scope of the appended claims.

What is claimed is:

1. A method for promoting healing of a dermal wound in animals and humans, comprising administering to an animal or a human affected by a dermal wound, an amount of soluble glucan which is therapeutically effective for promoting healing of a dermal wound, said soluble glucan which comprises a phosphorylated poly-[beta-(1-3) glucopyranose] chain which is characterized by:
   (i) the capability of dissolving in water or an aqueous solution;
   (ii) being non-toxic, non-immunogenic and substantially non-pyrogenic; and
   (iii) the capability of exerting a profound immunobiological response when administered in vivo to an animal or to a human.

2. A method for promoting healing of a dermal wound in animals and humans, comprising administering to an animal or a human affected by a dermal wound, an effective amount of a pharmaceutical composition which comprises (a) an amount of a soluble glucan which is therapeutically effective for promoting healing of a dermal wound, the soluble glucan which comprises a phosphorylated poly-[beta-(1-3)glucopyranose] chain which is characterized by:
   (i) the capability of dissolving in water or an aqueous solution;
   (ii) being non-toxic, non-immunogenic and substantially non-pyrogenic; and
   (iii) the capability of exerting a profound immunobiological response when administered in vivo to an animal or to a human;
and (b) a physiologically acceptable carrier.

3. The method according to claim 1, in which the soluble phosphorylated glucan is administered topically, intravenously, intraperitoneally, subcutaneously or orally.

4. The method according to claim 2, in which the soluble phosphorylated glucan is administered topically, intravenously, intraperitoneally, subcutaneously, or orally.

5. The method according to claim 1, in which the wound is a surgical wound, a pressure wound, a trauma wound, a burn wound, a diabetic ulcer, a venous stasis ulcer or a malignant ulceration.

6. The method according to claim 5, in which the pressure wound is a decubitus ulcer.

7. The method according to claim 2, in which the wound is a surgical wound, a pressure wound, a trauma wound, a burn wound, a diabetic ulcer, a venous stasis ulcer or a malignant ulceration.

8. The method according to claim 7, in which the pressure wound is a decubitus ulcer.

9. A method for promoting healing of a dermal wound in animals and humans, comprising administering to an animal or a human affected by a dermal wound, therapeutically effective amounts of (a) an antimicrobial agent; and (b) a soluble glucan which comprises a phosphorylated poly[beta-(1-3)glucopyranose] chain which is characterized by:
   (i) the capability of dissolving in water or an aqueous solution;
   (ii) being non-toxic, non-immunogenic and substantially non-pyrogenic; and
   (iii) the capability of exerting a profound immunobiological response when administered in vivo to an animal or to a human.

10. A method for promoting healing of a dermal wound in animals and humans, comprising administering to an animal or a human affected by a dermal wound, therapeutically effective amounts of (a) an anticancer agent; and (b) a soluble glucan which comprises a phosphorylated poly[beta-(1-3)glucopyranose] chain which is characterized by:
   (i) the capability of dissolving in water or an aqueous solution;
   (ii) being non-toxic, non-immunogenic and substantially non-pyrogenic; and
   (iii) the capability of exerting a profound immunobiological response when administered in vivo to an animal or to a human.

* * * * *